(12) United States Patent
Mayorga et al.

(10) Patent No.: US 7,968,001 B2
(45) Date of Patent: *Jun. 28, 2011

(54) STABILIZERS FOR THE STABILIZATION OF UNSATURATED HYDROCARBON-BASED PRECURSOR

(75) Inventors: Steven Gerard Mayorga, Oceanside, CA (US); Kelly Ann Chandler, San Marcos, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 84 days.

This patent is subject to a terminal disclaimer.

(21) Appl. No.: 12/038,409

(22) Filed: Feb. 27, 2008

(65) Prior Publication Data

US 2009/0159843 A1    Jun. 25, 2009

Related U.S. Application Data

(60) Provisional application No. 61/015,028, filed on Dec. 19, 2007.

(51) Int. Cl.
| | |
|---|---|
| *C09K 3/00* | (2006.01) |
| *C09K 15/00* | (2006.01) |
| *C09K 15/16* | (2006.01) |
| *C09K 15/22* | (2006.01) |
| *C07D 211/00* | (2006.01) |
| *C07D 295/00* | (2006.01) |

(52) U.S. Cl. ......... 252/182.29; 252/182.11; 252/182.12; 252/397; 252/401; 252/403; 546/184

(58) Field of Classification Search ............. 252/182.11, 252/182.12, 182.29, 397, 401, 403; 546/184
See application file for complete search history.

(56) References Cited

U.S. PATENT DOCUMENTS

| | | | | |
|---|---|---|---|---|
| 2,739,131 | A * | 3/1956 | Thompson et al. | ........... 252/403 |
| 4,992,493 | A * | 2/1991 | Cantatore et al. | ................ 524/97 |
| 5,019,614 | A * | 5/1991 | Klei | .............................. 524/100 |
| 5,731,129 | A * | 3/1998 | Koshimura et al. | ........ 430/286.1 |
| 6,121,358 | A * | 9/2000 | Dershem et al. | .............. 524/439 |
| 6,835,288 | B1 | 12/2004 | Sutoris et al. | |
| 2003/0149213 | A1* | 8/2003 | Mayorga et al. | ................ 528/10 |
| 2007/0057235 | A1 | 3/2007 | Teff | |

FOREIGN PATENT DOCUMENTS

| | | |
|---|---|---|
| EP | 0 959 059 A | 11/1999 |
| KR | 2002-0070302 A | 9/2002 |
| WO | 99/61396 A | 12/1999 |
| WO | 01/40149 A | 6/2001 |

OTHER PUBLICATIONS

Acros Organics: 2004/2005 Catalog of Organics and Fine Chemicals, p. 252 (2004).*

U.S. Appl. No. 60/943,867, filed Jun. 14, 2007, Steven Gerard Mayorga, et al.

* cited by examiner

*Primary Examiner* — Lorna M Douyon
*Assistant Examiner* — Tanisha Diggs
(74) *Attorney, Agent, or Firm* — Lina Yang (57) ABSTRACT

A stabilized composition consists essentially of unsaturated hydrocarbon-based materials, and a stabilizer selected from the group consisting of hydroxybenzophenone and a nitroxyl radical based stabilizer. A method for stabilizing unsaturated hydrocarbon-based precursor material against the polymerization comprises providing a stabilizer selected from the group consisting of a hydroxybenzophenone and a nitroxyl radical based stabilizer.

7 Claims, 3 Drawing Sheets

STABILIZERS FOR THE STABILIZATION OF UNSATURATED HYDROCARBON-BASED PRECURSOR

CROSS-REFERENCE TO RELATED APPLICATIONS

This application claims benefit of U.S. Provisional Application No. 61/015,028, filed Dec. 19, 2007. The disclosure of this provisional application is hereby incorporated by reference.

BACKGROUND OF THE INVENTION

Future generations of dielectric films utilize porogens in combination with organosilicates precursors to produce porous low k films. For this purpose saturated or unsaturated hydrocarbon-based porogens are co-deposited with the organosilicate to produce the initial composite film, comprising a mixture of organosilicate precursor and organic porogen. This film is subsequently subjected to various treatment methods to decompose the porogen. During this curing process the porogen byproducts are liberated as gaseous species leaving behind an organosilicate matrix containing voids in the spaces vacated by the porogen. The resulting voids or air pockets have an intrinsic dielectric constant of unity which has the effect of decreasing the overall dielectric constant of the porous solid below that of the dense matrix material.

Other areas in which organic precursors are being used in the microelectronics industry are the deposition of carbon hardmasks and the deposition of anti-reflective coatings. These films are deposited by plasma enhanced chemical vapor deposition (PECVD) using hydrocarbon precursors, especially unsaturated organic hydrocarbons.

Unsaturated hydrocarbon-based materials have been evaluated for use as a porogen precursor to be used along with an appropriate organosilicate precursor for the deposition of porous low k films.

However, many unsaturated hydrocarbons that are prone to polymerization will gradually degrade or polymerize at ambient temperature or at moderate temperatures that are often encountered during normal processing, purification or application of the particular chemical. The prior art discloses a variety of chemicals used to stabilize hydrocarbon-based porogens against the polymerization of olefinic hydrocarbons, including several broad classes of organic compounds such as phenols, amines, hydroxylamines, nitro compounds, quinine compounds and certain inorganic salts. An example of this would be monomers such as butadiene and isoprene which are well known to undergo gradual polymerization in storage tanks or during transportation at ambient temperatures.

Some of unsaturated hydrocarbon-based precursor materials are described in U.S. Pat. No. 6,846,515, commonly assigned to the assignee of the present invention, which is incorporated by reference herein in its entirety.

2,5-Norbornadiene (NBDE) is one of the leading materials being evaluated as a precursor for porogen, carbon hardmask and antireflective coating, for the production of low dielectric constant films using chemical vapor deposition (CVD) methods. Isoprene is a promising precursor for the deposition of carbon hardmasks and antireflective coatings. However, NBDE and isoprene are thermally unstable with respect to oligomerization/polymerization.

NBDE and isoprene degrade at a substantial rate at ambient temperature to form soluble NBDE and isoprene oligomeric degradation products. Isoprene is also known to undergo a relatively rapid dimerization reaction. Hence, the concentration of dissolved oligomers in NBDE and isoprene are expected to gradually increase over time during their transport and storage prior to their utilization as a precursor for dielectric materials. Furthermore, the soluble oligomers will immediately precipitate upon contact with a more polar liquid such as diethoxymethylsilane (DEMS). This instability is expected to cause precursor delivery problems and film quality issues.

Chemical vendors commonly supply NBDE with 100-1000 parts per million (ppm) of 2,6-di-tert-butyl-4-methylphenol, also known as butylated hydroxytoluene or by the acronym BHT. BHT is currently used as the industry standard to slow the rate of NBDE degradation for transport and storage purposes. However, BHT has limited efficacy to suppress NBDE degradation.

A recently published U.S. Patent Application 20070057235 by Teff et al. taught the use of phenolic antioxidants for the stabilization of NBDE.

In order for NBDE or isoprene to be viable in a manufacturing environment it is critical that the oligomer (i.e., nonvolatile residue) content is minimized to avoid processing issues and to allow manufacturers to meet the demanding film quality specifications as set by the semi-conductor industry.

This invention discloses effective stabilizers which can be used to slow down the rate of degradation for the unsaturated hydrocarbons precursors, thereby mitigating the potential process and film quality issues which can result from precursor instability, thus, increasing the viability of such materials for application as precursors for porogens, carbon hardmask materials and antireflective coatings for the production of high quality low dielectric constant films.

BRIEF SUMMARY OF THE INVENTION

One embodiment of the present invention is a stabilized composition consisting essentially of an unsaturated hydrocarbon-based precursor material, and a stabilizer selected from the group consisting of a hydroxybenzophenone based stabilizer and a nitroxyl radical based stabilizer.

Another embodiment of the present invention is a stabilized composition, consisting essentially of an unsaturated hydrocarbon-based material, at least one polar liquid and a stabilizer selected from the group consisting of a hydroxybenzophenone based stabilizer, a nitroxyl radical based stabilizer and a hydroquinone based stabilizer.

Another embodiment of the present invention is a stabilized composition, consisting essentially of 2,5-Norbornadiene (NBDE), and a stabilizer selected from the group consisting of a hydroxybenzophenone based stabilizer and a nitroxyl radical based stabilizer.

Yet, another embodiment of the present invention is a method for stabilizing an unsaturated hydrocarbon-based precursor material against polymerization. The method comprises providing a stabilizer selected from the group consisting of a hydroxybenzophenone based stabilizer and a nitroxyl radical based stabilizer.

Yet, another embodiment of the present invention is a method for stabilizing 2,5-Norbornadiene (NBDE) against its polymerization comprising providing a stabilizer selected from the group consisting of a hydroxybenzophenone based stabilizer and a nitroxyl radical based stabilizer.

Yet, another embodiment of the present invention is a method for stabilizing an unsaturated hydrocarbon-based precursor against precipitation of solids upon contact of the unsaturated hydrocarbon with at least one polar liquid, comprising

(a) adding to the unsaturated hydrocarbon-based precursor a stabilizer selected from the group consisting of a hydroxybenzophenone based stabilizer, a nitroxyl radical based stabilizer and a hydroquinone based stabilizer; and (b) contacting mixture in (a) with the at least one polar liquid.

For the embodiments above, the unsaturated hydrocarbon-based precursor material can have both cyclic or non-cyclic structure, wherein the cyclic structure is selected from the group consisting of (a) at least one singly or multiply unsaturated cyclic hydrocarbon having a formula $C_nH_{2n-2x}$, wherein x is a number of unsaturated sites, n is from 4 to 14, the number of carbons in the cyclic structure is between 4 and 10; and (b) at least one multiply unsaturated bicyclic hydrocarbon having a formula $C_nH_{2n-(2+2x)}$, wherein x is a number of unsaturated sites, n is from 4 to 14, the number of carbons in the bicyclic structure is from 4 to 12;

the hydroxybenzophenone based stabilizer is represented by a structure of:

wherein at least one member of the group $R^1$ through $R^{10}$ is hydroxyl, the remaining $R^1$ through $R^{10}$ is independently selected from the group consisting of hydrogen, hydroxyl, $C_1$-$C_{18}$ linear, branched or cyclic alkyl, $C_1$-$C_{18}$ linear, branched or cyclic alkenyl, $C_1$-$C_{18}$ linear, branched or cyclic alkoxy, substituted or unsubstituted $C_4$-$C_8$ aryl and combinations thereof;

the nitroxyl radical based stabilizer is represented by a structure having at least one NO group:

wherein:
raised period "■" denotes one unpaired electron;
$R^1$ through $R^4$ are independently selected from a straight chained or branched, substituted or unsubstituted, alkyl or alkenyl group having a chain length sufficient to provide steric hinderance for the NO group; wherein the substituted group comprises oxygen-containing groups selected from the group consisting of hydroxyl, carbonyl, alkoxide, and carboxylic group; and
$R^5$ and $R^6$ are independently selected from a straight chained or branched, a substituted or unsubstituted, alkyl group or alkenyl group.

Further for some of the embodiments above, the unsaturated hydrocarbon-based precursor material is selected from the group consisting of 2,5-Norbornadiene (NBDE) and isoprene; the nitroxyl radical based stabilizer is selected from the group consisting of 2,2,6,6-tetramethyl-1-piperidinyloxy (TEMPO), 4-hydroxy-2,2,6,6-tetramethyl-1-piperidinyloxy (4H-TEMPO) and combinations thereof; the hydroxybenzophenone based stabilizer is selected from the group consisting of 2-hydroxy-4-methoxy-benzophenone (2H4MB), 2,4-dihydroxybenzophenone (24DHB), 2,2'-dihyroxy-4-methoxybenzophenone (22DH4MB) and combinations thereof; the hydroquinone based stabilizer is selected from the group consisting of methyl hydroquinone (MHQ), hydroquinone monomethyl ether (HQMME) and combinations thereof; and the at least one polar liquid is selected from the group consisting of diethoxymethylsilane (DEMS), isopropanol (IPA) and the mixture thereof.

DETAILED DESCRIPTION OF THE INVENTION

The unsaturated hydrocarbon-based precursor material can be cyclic unsaturated hydrocarbon-based.

The cyclic unsaturated hydrocarbon-based precursor material can be singly or multiply unsaturated cyclic hydrocarbon having a cyclic structure and the formula $C_nH_{2n-2x}$, where x is the number of unsaturated sites, n is 4 to 14, the number of carbons in the cyclic structure is between 4 and 10, and at least one singly or multiply unsaturated cyclic hydrocarbon optionally contains a plurality of simple or branched hydrocarbons substituents substituted onto the cyclic structure, and contains unsaturation inside endocyclic or on one of the hydrocarbon substituents. Examples include cyclohexene, vinylcyclohexane, dimethylcyclohexene, t-butylcyclohexene, alpha-terpinene, pinene, 1,5-dimethyl-1,5-cyclooctadiene, and vinyl-cyclohexene.

The cyclic unsaturated hydrocarbon-based precursor material can also be multiply unsaturated bicyclic hydrocarbons of the general formula $C_nH_{2n-(2+2x)}$ where x is the number of unsaturated sites in the molecule, n=4-14, where the number of carbons in the bicyclic structure is between 4 and 12, and where there can be a plurality of simple or branched hydrocarbons substituted onto the cyclic structure. The unsaturation can be located inside endocyclic or on one of the hydrocarbon substituents to the cyclic structure. Examples include camphene, norbornene, norbornadiene, etc.

The unsaturated hydrocarbon-based precursor material can also be non-cyclic, such as linear hydrocarbon-based. An example of non-cyclic unsaturated hydrocarbon-based precursor material is isoprene.

Preferably, NBDE and isoprene are selected as the precursors for the production of low k dielectric materials.

NBDE (2,5-Norbornadiene) is a particularly attractive precursor candidate because of its high degree of chemical unsaturation which is believed to give rise to favorable deposition properties such as high deposition rates and high utilization efficiencies. The utilization efficiency pertains to the amount of hydrocarbon porogen precursor required relative to the organosilicate precursor in order to deposit a porous low k film of a given dielectric constant. Unfortunately, the high degree of unsaturation of NBDE may also be responsible for its intrinsic thermal instability with respect to oligomerization.

Laboratory evaluation has shown that NBDE degrades at ambient temperature to form soluble oligomeric species. The degradation products have been identified by solids-probe mass spectrometry to be a mixture of NBDE oligomers, including various dimers, trimers, tetramers, pentamers, hexamers, etc. shown in FIG. 1.

The degradation of NBDE raises a number of issues for its application as a precursor for making low k films. The high rate of degradation suggests that the chemical composition and physical properties of the precursor will change over time. Such changes are likely to have a significant impact on the properties of the resulting film, making it difficult for end users to produce a consistent quality film that conforms to the rigorous production specifications of thin film manufacturers.

A second problem posed by the NBDE and isoprene degradation is related the chemical delivery method commonly used for such liquid precursors. Volatile liquids such as NBDE and isoprene are often delivered by a technique referred to in the industry as DLI, or direct liquid injection. For DLI systems the precursor is delivered to the tool at a precisely metered rate as a liquid through an injector port into the heated injection manifold. The manifold is operated at elevated temperature and reduced pressure to cause the precursor to rapidly vaporize. Once vaporized, the gaseous precursor is delivered to the deposition chamber. The DLI delivery method will indiscriminately transfer the NBDE or isoprene liquid along with any dissolved oligomeric degradation products to the tool. The oligomers are expected to be either less volatile or non-volatile under the temperature and pressure conditions of the heated injection manifold. The delivery of low volatility oligomeric components would result in the gradual accumulation of said species in the tool plumbing which is expected to have a detrimental impact on tool operation and/or film quality.

A third possible negative consequence of using degraded NBDE is related to possible on-tool precipitation issues that may result from contact of partially degraded NBDE with a more polar chemical, such as DEMS (diethoxymethylsilane). Instantaneous precipitation of the oligomers is expected to occur if NBDE containing an appreciable concentration of dissolved oligomeric degradation products comes into contact with a substantial amount of a more polar liquid, such as an alcohol or an alkoxysilane such as DEMS. This effect is demonstrated in Examples 24, 25 and 30. The precipitation is believed to be caused by an increase in the overall polarity of the liquid blend that occurs when a substantial quantity of DEMS is added to NBDE. On-tool precipitation is expected to occur in the event that NBDE, containing oligomeric degradation products, comes into contact with a more polar component, such as DEMS, during the co-deposition of porogen and silica source materials. Such on-tool precipitation would cause increased tool down-time and/or necessitate more frequent tool preventative maintenance in order to avoid precursor plugging or flow problems. Oligomer precipitation may also cause indirect problems by adversely impacting film quality, and/or increasing on-wafer particle count, etc.

In order for precursor materials to be viable in a manufacturing environment they need to satisfy practical requirements with respect to product shelf-life. The product shelf life provides the end user or manufacturer assurance that the subject chemical will meet certain minimal standards of performance if used within the time allotted by the shelf-life specification. In practice the product shelf life is often defined by the length of time a chemical will meet pre-determined purity requirements with respect to key chemical components. The rate of NBDE and isoprene degradation must be reduced to an acceptable level to ensure that they conform to minimal shelf-life criteria, and as such, will be viable in a manufacturing environment as precursors for the production of low k films.

Figure 2:
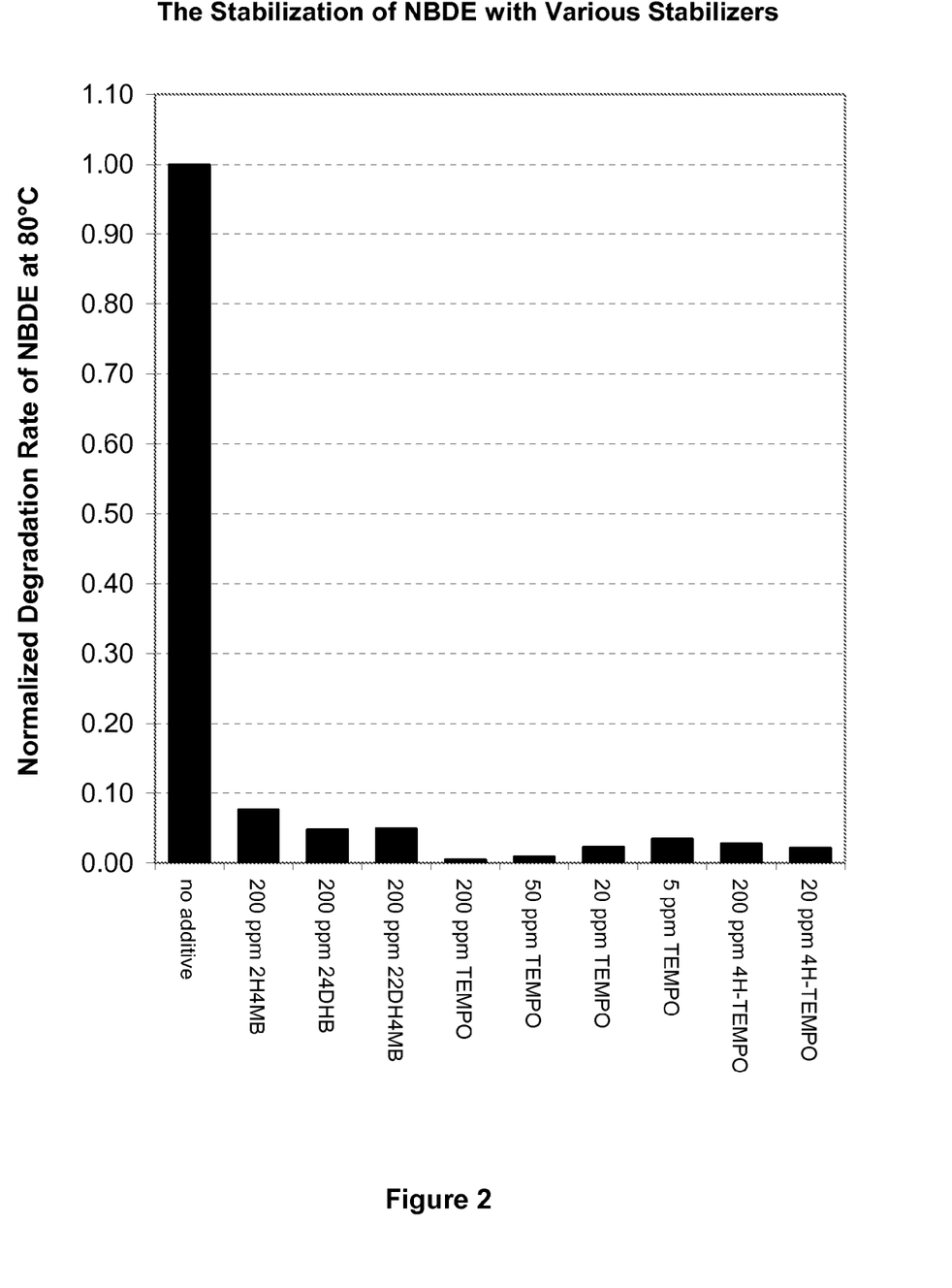
FIG. 2. The effect of different stabilizers from the present invention on the degradation rate of NBDE at 80° C.
Figure 3:
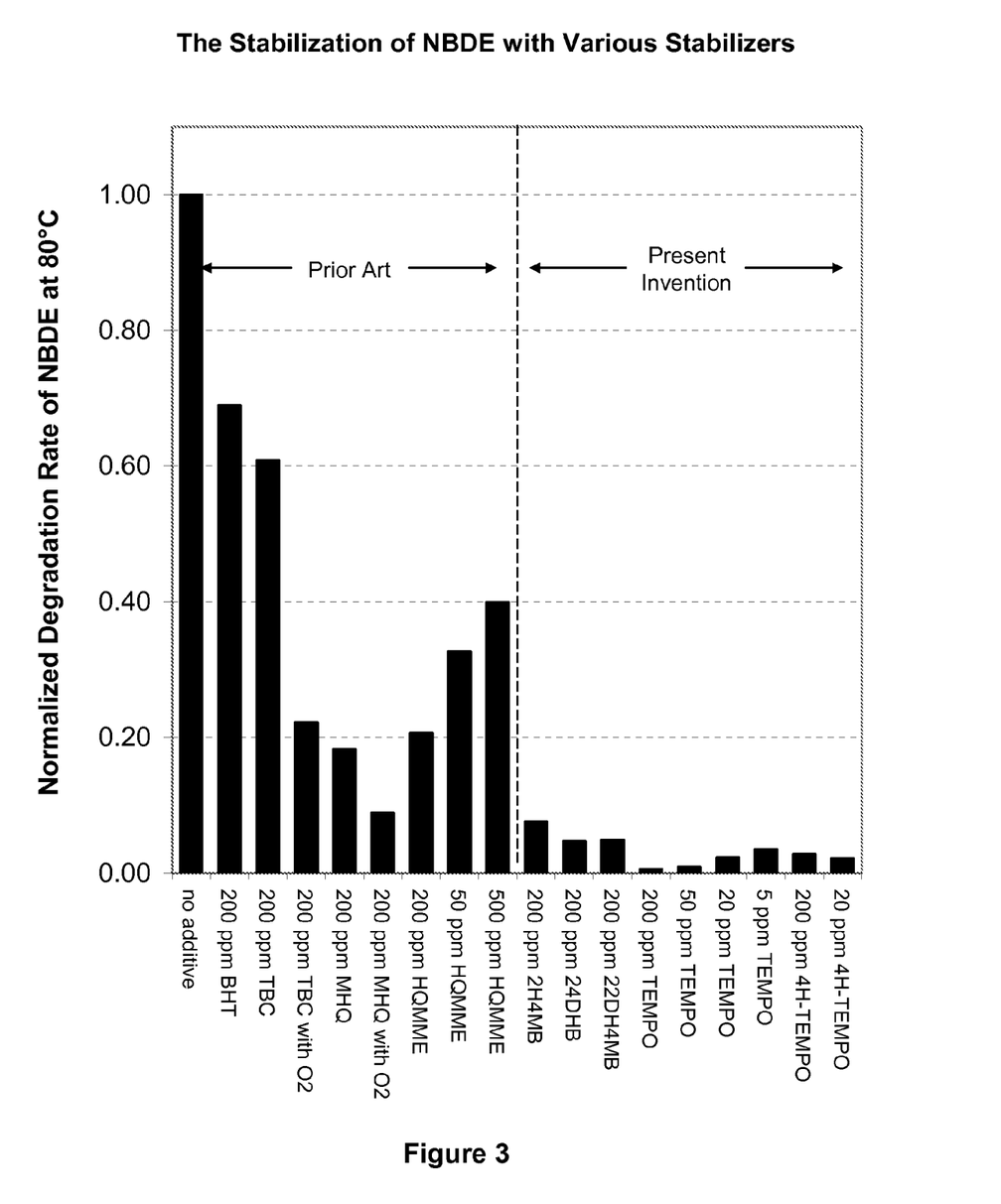
FIG. 3. The effect of different stabilizers on the degradation rate of NBDE at 80° C.; the stabilizers from the present invention were shown on the right and the stabilizers used in prior art were shown on the left.

Our laboratory tests have shown that NBDE degrades in the manner previously described at a rate of ~1.4 wt. % per year at ambient temperature, which corresponds to 1.6 ppm per hour. At 80° C. the rate of degradation increases 160-fold to 258 ppm/hr. Spiking NBDE with 200 ppm of BHT (usually provided by the chemical vendors) will reduce its rate of degradation by only 31%, such that it degrades at 179 ppm/hr at 80° C. Therefore, although BHT does slow down the degradation rate of NBDE, it does not slow it down enough to make it practical for use in the current application. These experiments are described in Examples 2-4 and summarized in Table 1 and FIGS. 2 and 3.

Our laboratory testing of the stabilizers MHQ and HQMME specified in US Patent Application 20070057235 by Teff et al. showed that they were indeed more effective than BHT for inhibiting polymerization of NBDE. For example, 200 ppm of MHQ decreased the degradation rate NBDE to 53 ppm per hour at 80° C.; 200 ppm of HQMME was slightly more effective dropping the degradation rate to 47 ppm per hour at 80° C. These represent 79% and 82% reduction, respectively, in the rate of degradation relative to the unstabilized NBDE. MHQ and HQMME were thus confirmed to be more effective than BHT for stabilizing NBDE, the same level of the latter inhibitor only decreased the NBDE degradation rate by 31% under comparable test conditions. Therefore, although MHQ and HQMME were more effective than BHT, they also have limited ability to suppress the oligomerization of NBDE, and as such, have limited utility for the stabilization of NBDE for the current application. These experiments are described in Examples 4, 7 and 9 and summarized in Table 1 and FIG. 3.

In the present invention two classes of materials are disclosed which are very effective for stabilizing NBDE. These two classes of materials are: hydroxybenzophenones and nitroxyl radicals. These two classes of inhibitors, unlike the quinones or phenolic antioxidants, do not require the presence of oxygen in order to be optimally effective.

The first class of stabilizers is known as hydroxybenzophenones. The hydroxybenzophenones are known to be light stabilizers which are active UV absorbers. They are not known for their ability to suppress the oligomerization reaction of thermally unstable unsaturated hydrocarbons. This class of stabilizers is represented by the following structure:

where at least one member of the group $R^1$ through $R^{10}$ is OH, the remaining $R^1$ through $R^{10}$ can each be hydrogen, hydroxyl, $C_1$-$C_{18}$ linear, branched, or cyclic alkyl, $C_1$-$C_{18}$ linear, branched, or cyclic alkenyl, $C_1$-$C_{18}$ linear, branched, or cyclic alkoxy, or substituted or unsubstituted $C_4$-$C_8$ aryl. Suitable examples of $R^1$ through $R^{10}$ may include but are not limited to hydrogen, hydroxyl, methyl, ethyl, n-propyl, n-butyl, iso-propyl, iso-butyl, tert-butyl, methoxy, ethoxy, propoxy, iso-propoxy, butoxy, iso-butoxy or tert-butoxy.

Suitable examples of the hydroxybenzophenone based stabilizers may include but are not limited to 2-hydroxy-4-(n-octyloxy)benzophenone, 2-hydroxy-4-methoxybenzophenone (2H4MB), 2,4-dihydroxybenzophenone (24DHB), 2-hydroxy-4-(n-dodecyloxy)benzophenone, 2,2'-dihyroxy-4-methoxybenzophenone(22DH4MB), 2,2'-dihydroxy-4,4'-dimethoxybenzophenone, 2,2',4,4'-tetrahydroxybenzophenone, 4-hydroxybenzophenone and any combination thereof.

Examples of preferred hydroxybenzophenones are 2-hydroxy-4-methoxybenzophenone (2H4MB), 2,4-dihydroxybenzophenone (24DHB), and 2,2'-dihyroxy-4-methoxybenzophenone (22DH4MB).

The amount of the stabilizer is preferably from 1 to 5000 parts per million (ppm), more preferably 5 to 1000 ppm, and most preferable 20 to 200 ppm.

In preferred embodiments, NBDE or isoprene is selected as the unsaturated hydrocarbon-based precursor for the production of low k dielectric materials; 2-hydroxy-4-methoxy-benzophenone, 2,4-dihydroxybenzophenone, or 2,2'-dihyroxy-4-methoxybenzophenone is selected as the hydroxybenzophenone based stabilizer. The amount of the stabilizer is from 20 to 200 ppm. The stabilizers in the preferred embodiments described herein, are shown to be considerably more effective at suppressing the rate of degradation than those disclosed in the prior art, and as such, increase the likelihood of the successful commercial implementation of the precursors for the production of low k dielectric materials.

The second class of stabilizers known as nitroxyl radicals is represented by the following structure:

Such nitroxyl radical compounds have at least one NO, wherein
the raised period "■" denotes one unpaired electron,
the nitrogen atom is further bound to two carbon atoms,
$R^1$ through $R^4$ are the same or different, straight chained or branched, substituted or unsubstituted, alkyl or alkenyl groups of a chain length sufficient to provide steric hinderance for the NO group, in which the substituted constituents may comprise oxygen-containing groups such as hydroxyls, carbonyls, alkoxides, carboxylic groups, including substituted groups, thereof;
$R^5$ and $R^6$ are the same or different, straight chained or branched, substituted or unsubstituted, alkyl or alkenyl groups, which may be further connected by various bridging groups to form cyclic structures, such as, which may have fused to it another saturated, partially unsaturated or aromatic ring, in which any of the aforementioned cyclic or ring structures may possess ring substituents such as straight chain or branched alkyl groups or oxygen-containing groups such as hydroxyls, carbonyls, alkoxides, carboxylic groups, including substituted groups, thereof.

Suitable examples of $R^1$ through $R^4$ include but are not limited to methyl, ethyl, n-propyl, n-butyl, n-pentyl, iso-propyl, iso-butyl, iso-pentyl, tert-butyl, neo-pentyl, octadecyl, propenyl, butenyl, pentenyl, and the like.

Suitable examples of $R^5$ and $R^6$ include but are not limited to methyl, ethyl, n-propyl, n-butyl, n-pentyl, iso-propyl, iso-butyl, iso-pentyl, tert-butyl, neo-pentyl, octadecyl, ethenyl, propenyl, butenyl, pentenyl, or $R^5$ and $R^6$ may constitute part of a cyclic structure, such as the 6-membered piperidines, 5-membered pyrrolidones and the like, examples of which are provided below. These ring structures may be substituted.

Suitable examples of the nitroxyl radical based stabilizers include but are not limited to 2,2,6,6-tetramethyl-1-piperidinyloxy (TEMPO) and 4-hydroxy-2,2,6,6-tetramethyl-1-piperidinyloxy (4H-TEMPO), di-tert-butyl nitroxyl, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl 4-tert-butyl benzoate, bis(1-oxyl-2,2,6,6-tetramethylpiperidin-4-yl)succinate, bis(1-oxyl-2,2,6,6-tetramethylpiperidin-4-yl)adipate, bis(1-oxyl-2,2,6,6-tetramethylpiperidin-4-yl)sebacate, bis(1-oxyl-2,2,6,6-tetramethylpiperidin-4-yl)n-butylmalonate, bis(1-oxyl-2,2,6,6-tetramethylpiperidin-4-yl)phthalate, bis(1-oxyl-2,2,6,6-tetramethylpiperidin-4-yl)isophthalate, bis(1-oxyl-2,2,6,6-tetramethylpiperidin-4-yl)terephthalate, bis(1-oxyl-2,2,6,6-tetramethylpiperidin-4-yl)hexahydroterephthalate, N,N'-bis(1-oxyl-2,2,6,6-tetramethylpiperidin-4-yl)adipamide, N-(1-oxyl-2,2,6,6-tetramethylpiperidin-4-yl)-caprolactam, N-(1-oxyl-2,2,6,6-tetramethylpiperidin-4-yl)-dodecylsuccinimide, 2,4,6-tris(1-oxyl-2,2,6,6-tetramethylpiperidin-4-yl isocyanurate, 2,4,6-tris-[N-butyl-N-(1-oxyl-2,2,6,6-tetramethylpiperidin-4-yl]-s-triazine, and 4,4'-ethylenebis(1-oxyl-2,2,6,6-tetramethyl piperazin-3-one).

Examples of preferred nitroxyl radicals are TEMPO and 4H-TEMPO. The structures of these two compounds are shown below.

TEMPO                4H-TEMPO

The amount of the stabilizer is preferably from 1 to 5000 parts per million (ppm), more preferably 5 to 1000 ppm, and most preferable 20 to 200 ppm.

In preferred embodiments, NBDE or isoprene is selected as the unsaturated hydrocarbon-based precursor for the production of low k dielectric materials and TEMPO or 4H-TEMPO is selected as the nitroxyl radical based stabilizer. The amount of the stabilizer is from 20 to 200 ppm. The stabilizers in the preferred embodiments described herein, are shown to be considerably more effective at suppressing the rate of degradation of NBDE than those disclosed in the prior art, and as such, increase the likelihood of its commercial implementation for the production of porous low k dielectric materials.

WORKING EXAMPLES

In order to more fully describe the present invention, the following examples are presented which are intended to be merely illustrative and not in any sense limitative of the invention.

NBDE degrades at a substantial rate at ambient temperature forming soluble oligomeric byproducts. The degradation may or may not result in the discoloration of the NBDE liquid. The extent of degradation is assessed by determining the concentration of oligomers in the NBDE liquid. However, gas chromatography, the most common chemical analysis method used for organic liquids, is not an effective method for quantifying the amount of oligomers in NBDE solution. The oligomers cannot be accurately quantified by GC because they are reactive and, as such, they are prone to further oligomerization. They are also generally non-volatile because of their high molecular weight causing them to elute from the GC column only after very long retention times or perhaps not at all.

A non-volatile residue test has been developed to reliably measure the amount of oligomers in NBDE solution. To perform this evaluation NBDE is evaporated by purging the NBDE container with a high purity inert gas, such as helium, leaving behind the non-volatile residue components. The container may be heated slightly during the evaporation step in order to obtain a stable final weight. The weight of the non-volatile residue, thus determined, is used as a measure of the amount of oligomers in solution, and hence, an indication of the extent of degradation of NBDE. This general method is described in further detail in Example 1.

Unstabilized NBDE degrades at a rate of approximately 1.4% per year at ambient temperature. This corresponds to about 270 ppm per week or about 1.6 ppm per hour. In order to assess the relative degradation within a practical period of time, various samples of unstabilized and stabilized NBDE were subjected to standardized accelerated aging test conditions. This test consisted of distilling the NBDE to remove any non-volatile degradation products. Within 24 hours the distilled NBDE was placed into quartz containers as described below, and heated to 60-80° C. for 6-7 days. After this time the containers were cooled to room temperature and the amount of degradation was determined. In this manner various stabilizers were assessed according to their relative ability to suppress the degradation of NBDE. Examples 2-23, illustrate the measurement of non-volatile residue (i.e., the extent of degradation) for various samples of neat and stabilized NBDE. The NBDE used in Example 2 was aged at room temperature. The NBDE evaluated in Examples 3-23 was subjected to accelerated aging conditions as described herein.

Example 1

Residue Evaluation of Recently Distilled NBDE

A sample of NBDE was flash distilled to remove non-volatile impurities using a rotary-evaporator. The distilled material was analyzed by GC to have a nominal purity of 99.4%. The tare weight of an empty, clean 1.2 liter quartz bubbler was recorded after evacuation. The bubbler was previously equipped with gas inlet and outlet ports, each fitted with a Teflon valve. The bubbler inlet port had a dip-tube that extends to within ⅛" of the base of the container. About 600 g of NBDE was added to the quartz bubbler within a nitrogen-containing dry box. The bubbler was re-weighed to determine the weight of the NBDE. A cylinder of research grade He was connected to the bubbler inlet line. The bubbler temperature was increased to 35° C. to increase the vapor pressure of the NBDE. He was purged through the bubbler at a flow rate of 3.0 SLPM (standard liters per minute) for 4 hours to evaporate the NBDE. At this time the bubbler temperature was raised to 80° C. and the bubbler was evacuated for 2.0 hours to achieve a stable weight. This experiment was done in duplicate. The weights of the non-volatile residue for the two runs were 0.59 g and <0.01 g, corresponding to an average residue of 0.05 wt. %. The experimental results are summarized in Table 1.

Example 2

Evaluation of the Degradation Rate of NBDE Stored at Ambient Temperature

A 13.0 liter sample of NBDE was purified by atmospheric distillation. The distilled sample was analyzed by GC to have a nominal purity of 99.4%. The sample was stored in a chemical cabinet indoors for a total of 287 days. At this time approximately 200 g of NBDE was loaded into a pre-cleaned, pre-tared bubbler as described in Example 1. The bubbler was subjected to 3.0 SLPM at 35° C. for 4.0 hours to evaporate the NBDE. The bubbler temperature was raised to 80° C. and the bubbler was evacuated for 2.0 hours to achieve a stable weight. The final weight of the bubbler was recorded after the evacuation step to determine the weight of the non-volatile residue. This experiment was done in duplicate. The weights of the non-volatile residue for the two runs were 2.29 g and 2.24 g, corresponding to an average residue of 1.12 wt. %. This is equivalent to a degradation rate of 1.63 ppm per hour based on the weight of the residue and the 287 days of aging. The experimental results are summarized in Table 1.

Example 3

Evaluation of the Degradation Rate of Unstabilized NBDE Using Accelerated Aging Conditions A sample of NBDE was flash distilled to remove non-volatile impurities as described in Example 1. Approximately 150-200 g of the distilled NBDE was loaded into a cleaned, pre-tared bubbler as described in Example 1. The bubbler was placed into an oven and held at 80° C. for 7 days. The temperature of 80° C. was chosen for this study for two reasons: (1) 7 days at 80° C. is intended to simulate the amount of degradation that would occur if the sample were allowed to age at ambient temperature for 1 year, assuming that the degradation rate follows a simple Arrhenius type behavior of doubling for every temperature increase of 10° C.; and (2) 80° C. is a common temperature for the heated manifold used to vaporize precursors prior to the mixing bowl and/or deposition chamber in chemical vapor deposition hardware. The quartz bubbler was removed from the 80° C. oven after 7 days. The bubbler was held at 35° C. while purging with 3 SLPM of He for 6 hours. At this time the bubbler temperature was raised to 80° C. and the bubbler was evacuated for 2.0 hours to achieve a stable weight. The final weight of the bubbler was recorded after the evacuation step to determine the weight of the non-volatile residue. This experiment was run a total of 6 times, since it was used as the "control" for the evaluation of various stabilizers. The average non-volatile residue for these runs was 4.33 wt. %, corresponding to a degradation rate of 258 ppm per hour at 80° C. The experimental results are summarized in Table 1 and FIGS. 2 and 3.

Example 4

Evaluation of the Degradation Rate of NBDE Stabilized with 200 ppm of BHT Using Accelerated Aging Conditions Commercial samples of NBDE are typically stabilized with BHT. In this example, comparable experiments were carried out to evaluate the degradation rate of NBDE when using BHT as the stabilizer.

A sample of NBDE was flash distilled to remove non-volatile impurities as described in Example 1. The distilled NBDE was spiked with 200 ppm by weight of BHT stabilizer. This is a common level of BHT present in NBDE as provided by chemical suppliers. The stabilized NBDE was subjected to accelerated aging test conditions by heating to 80° C. for 7 days, followed by He purge to determine the amount of non-volatile residue as described in Example 3. This test was run in duplicate. The average non-volatile residue for these two runs was 2.64 wt. %, corresponding to a degradation rate of 179 ppm per hour at 80° C. This represents a 31% decrease in the degradation rate relative to unstabilized NBDE. The experimental results are summarized in Table 1 and FIG. 3.

Example 5

Evaluation of the Degradation Rate of NBDE Stabilized with 200 ppm of TBC using Accelerated Aging Conditions A sample of NBDE was flash distilled to remove non-volatile impurities as described in Example 1. The distilled NBDE was spiked with 200 ppm by weight of TBC (p-tert-butylcatechol) stabilizer. The stabilized NBDE was subjected to accelerated aging test conditions by heating to 80° C. for 7 days, followed by He purge to determine the amount of non-volatile residue as described in Example 3. This test was run in duplicate. The average non-volatile residue for these two runs was 2.64 wt. %, corresponding to a degradation rate of 157 ppm per hour at 80° C. This represents a 39.1% decrease in the degradation rate relative to unstabilized NBDE. The experimental results are summarized in Table 1 and FIG. 3.

Example 6

Evaluation of the Degradation Rate of NBDE Stabilized with 200 ppm of TBC Containing 8 Volume % Oxygen in the Headspace The utilization of oxygen in combination with the stabilizer is typically done to enhance stability during chemical transport and storage. This is accomplished by storing the polymerizable chemical in a container in which oxygen comprises 5-20% of the gas in the headspace above the stored liquid. In this manner, the oxygen dissolves in the hydrocarbon liquid and thus is available to facilitate the inhibition of the polymerization reaction. The oxygen can be diluted with an inert gas such as nitrogen or helium to create the desired oxygen content in the headspace gas. This is commonly done to ensure a non-flammable environment for the material being stabilized. Alternatively, an appropriate amount of ambient air can be introduced into the container in order to establish the desired gaseous oxygen content.

A sample of NBDE was flash distilled to remove non-volatile impurities as described in Example 1. The distilled NBDE was spiked with 200 ppm by weight of TBC stabilizer. Approximately 170 g (~200 ml) of TBC-stabilized NBDE was added to a 500 ml quartz bubbler within a nitrogen dry box as described in Example 1. The bubbler was removed from the dry box. Twenty five sccm (standard cubic centimeters) of nitrogen was removed from the bubbler headspace using a syringe. Twenty five sccm of research grade oxygen was subsequently added to the headspace by reinjecting the gas into the bubbler. The NBDE bubbler thus prepared had nominally 8 volume percent oxygen in the headspace. The sample was subjected to accelerated aging test conditions by heating to 80° C. for 7 days, followed by He purge to determine the amount of non-volatile residue as described in Example 3. This test was run in duplicate. The average non-volatile residue for these two runs was 0.97 wt. %, corresponding to a degradation rate of 57 ppm per hour at 80° C. This represents a 77.7% decrease in the degradation rate relative to unstabilized NBDE. The experimental results are summarized in Table 1 and FIG. 3.

Example 7

Evaluation of the Degradation Rate of NBDE Stabilized with 200 ppm of MHQ Using Accelerated Aging Conditions A sample of NBDE was flash distilled to remove non-volatile impurities as described in Example 1. The distilled NBDE was spiked with 200 ppm by weight of MHQ (methyl hydroquinone) stabilizer. The stabilized NBDE was subjected to accelerated aging test conditions by heating to 80° C. for 7 days, followed by He purge to determine the amount of non-volatile residue as described in Example 3. This test was run in duplicate. The average non-volatile residue for these two runs was 0.79 wt. %, corresponding to a degradation rate of 47 ppm per hour at 80° C. This represents an 81.7% decrease in the degradation rate relative to unstabilized NBDE. The experimental results are summarized in Table 1 and FIG. 3

Example 8

Evaluation of the Degradation Rate of NBDE Stabilized with 200 ppm of MHQ Containing 5 Volume % Oxygen in the Headspace A sample of NBDE was flash distilled to remove non-volatile impurities as described in Example 1. The distilled NBDE was spiked with 200 ppm by weight of MHQ stabilizer. Approximately 150 g (~180 ml) of MHQ-stabilized NBDE was added to a 500 ml quartz bubbler within a nitrogen dry box as described in Example 1. The bubbler was removed from the dry box. Sixteen sccm (standard cubic centimeters) of nitrogen was removed from the bubbler headspace using a syringe. Sixteen sccm of research grade oxygen was subsequently added to the headspace by reinjecting the gas into the bubbler. The NBDE bubbler thus prepared had nominally 5 volume percent oxygen in the headspace. The stabilized NBDE was subjected to accelerated aging test conditions by heating to 80° C. for 7 days, followed by He purge to determine the amount of non-volatile residue as described in Example 3. This test was run in duplicate. The average non-volatile residue for these two runs was 0.39 wt. %, corresponding to a degradation rate of 23 ppm per hour at 80° C. This represents a 91.1% decrease in the degradation rate relative to unstabilized NBDE. The experimental results are summarized in Table 1 and FIG. 3.

Example 9

Evaluation of the Degradation Rate of NBDE Stabilized with 200 ppm of HQMME Using Accelerated Aging Conditions A sample of NBDE was flash distilled to remove non-volatile impurities as described in Example 1. The distilled NBDE was spiked with 200 ppm by weight of HQMME (hydroquinone monomethyl ether) stabilizer. The stabilized NBDE was subjected to accelerated aging test conditions by heating to 80° C. for 7 days, followed by He purge to determine the amount of non-volatile residue as described in Example 3. This test was run in duplicate. The average non-volatile residue for these two runs was 0.90 wt. %, corresponding to a degradation rate of 53 ppm per hour at 80° C. This represents a 79.3% decrease in the degradation rate relative to unstabilized NBDE. The experimental results are summarized in Table 1 and FIG. 3.

Example 10

Evaluation of the Degradation Rate of NBDE Stabilized with 50 ppm of HQMME Using Accelerated Aging Conditions A sample of NBDE was flash distilled to remove non-volatile impurities as described in Example 1. The distilled NBDE was spiked with 50 ppm by weight of HQMME stabilizer. The stabilized NBDE was subjected to accelerated aging test conditions by heating it to 80° C. for 7 days, followed by He purge to determine the amount of non-volatile residue as described in Example 3. This test was run in duplicate, using 111 g and 130 g of NBDE for the two runs. The average non-volatile residue for these two runs was 1.42 wt. %, corresponding to a degradation rate of 84 ppm per hour at 80° C. This represents a 67.3% decrease in the degradation rate relative to unstabilized NBDE. The experimental results are summarized in Table 1 and FIG. 3.

Example 11

Evaluation of the Degradation Rate of NBDE Stabilized with 500 ppm of HQMME Using Accelerated Aging Conditions A sample of NBDE was flash distilled to remove non-volatile impurities as described in Example 1. The distilled NBDE was spiked with 500 ppm by weight of HQMME stabilizer. The stabilized NBDE (209 g) was subjected to accelerated aging test conditions by heating to 80° C. for 7 days, followed by He purge to determine the amount of non-volatile residue as described in Example 3. The non-volatile residue for this run was measured to be 1.73 wt. %, corresponding to a degradation rate of 103 ppm per hour at 80° C. This represents a 60.1% decrease in the degradation rate relative to unstabilized NBDE. The experimental results are summarized in Table 1 and FIG. 3.

Example 12

Evaluation of the Degradation Rate of NBDE Stabilized with 200 ppm of 2-hydroxy-4-methoxybenzophenone (2H4MB) Using Accelerated Aging Conditions A sample of NBDE was flash distilled to remove non-volatile impurities as described in Example 1. The distilled NBDE was spiked with 200 ppm by weight of 2H4MB stabilizer. The stabilized NBDE was subjected to accelerated aging test conditions by heating to 80° C. for 7 days, followed by He purge to determine the amount of non-volatile residue as described in Example 3. This test was run in duplicate. The average non-volatile residue for these two runs was 0.33 wt. %, corresponding to a degradation rate of 20 ppm per hour at 80° C. This represents a 92.3% decrease in the degradation rate relative to unstabilized NBDE. The experimental results are summarized in Table 1 and FIGS. 2 and 3.

Example 13

Evaluation of the Degradation Rate of NBDE Stabilized with 200 ppm of 2,4-dihydroxybenzophenone (24DHB) Using Accelerated Aging Conditions A sample of NBDE was flash distilled to remove non-volatile impurities as described in Example 1. The distilled NBDE was spiked with 200 ppm by weight of 24DHB stabilizer. The stabilized NBDE was subjected to accelerated aging test conditions by heating to 80° C. for 7 days, followed by He purge to determine the amount of non-volatile residue as described in Example 3. This test was run in duplicate. The average non-volatile residue for these two runs was 0.21 wt. %, corresponding to a degradation rate of 12 ppm per hour at 80° C. This represents a 95.2% decrease in the degradation rate relative to unstabilized NBDE. The experimental results are summarized in Table 1 and FIGS. 2 and 3.

Example 14

Evaluation of the Degradation Rate of NBDE Stabilized with 200 ppm of 2,2'-dihyroxy-4-methoxybenzophenone (22DH4MB) Using Accelerated Aging Conditions A sample of NBDE was flash distilled to remove non-volatile impurities as described in Example 1. The distilled NBDE was spiked with 200 ppm by weight of 22DH4MB stabilizer. The stabilized NBDE was subjected to accelerated aging test conditions by heating to 80° C. for 7 days, followed by He purge to determine the amount of non-volatile residue as described in Example 3. This test was run in duplicate. The average non-volatile residue for these two runs was 0.21 wt. %, corresponding to a degradation rate of 13 ppm per hour at 80° C. This represents a 95.1% decrease in the degradation rate relative to unstabilized NBDE. The experimental results are summarized in Table 1 and FIGS. 2 and 3.

Example 15

Evaluation of the Degradation Rate of NBDE at 80° C. Stabilized with 200 ppm of TEMPO Using Accelerated Aging Conditions A sample of NBDE was flash distilled to remove non-volatile impurities as described in Example 1. The distilled NBDE was spiked with 200 ppm by weight of TEMPO stabilizer. The stabilized NBDE was subjected to accelerated aging test conditions by heating to 80° C. for 7 days, followed by He purge to determine the amount of non-volatile residue as described in Example 3. This test was run in duplicate. The average non-volatile residue for these two runs was 0.02 wt. %, corresponding to a degradation rate of 1 ppm per hour at 80° C. This represents a 99.4% decrease in the degradation rate relative to unstabilized NBDE. The experimental results are summarized in Table 1 and FIGS. 2 and 3.

Example 16

Evaluation of the Degradation Rate of NBDE at 80° C. Stabilized with 50 ppm of TEMPO Using Accelerated Aging Conditions A sample of NBDE was flash distilled to remove non-volatile impurities as described in Example 1. The distilled NBDE was spiked with 50 ppm by weight of TEMPO stabilizer. The stabilized NBDE was subjected to accelerated aging test conditions by heating to 80° C. for 7 days, followed by He purge to determine the amount of non-volatile residue as described in Example 3. This test was run in duplicate. The average non-volatile residue for these two runs was 0.04 wt. %, corresponding to a degradation rate of 3 ppm per hour at 80° C. This represents a 99.0% decrease in the degradation rate relative to unstabilized NBDE. The experimental results are summarized in Table 1 and FIGS. 2 and 3.

Example 17

Evaluation of the Degradation Rate of NBDE at 80° C. Stabilized with 20 ppm of TEMPO Using Accelerated Aging Conditions A sample of NBDE was flash distilled to remove non-volatile impurities as described in Example 1. The distilled NBDE was spiked with 20 ppm by weight of TEMPO stabilizer. The stabilized NBDE was subjected to accelerated aging test conditions by heating to 80° C. for 7 days, followed by He purge to determine the amount of non-volatile residue as described in Example 3. This test was run in duplicate. The average non-volatile residue for these two runs was 0.10 wt. %, corresponding to a degradation rate of 6 ppm per hour at 80° C. This represents a 97.7% decrease in the degradation rate relative to unstabilized NBDE. The experimental results are summarized in Table 1 and FIGS. 2 and 3.

Example 18

Evaluation of the Degradation Rate of NBDE at 80° C. Stabilized with 5 ppm of TEMPO Using Accelerated Aging Conditions A sample of NBDE was flash distilled to remove non-volatile impurities as described in Example 1. The distilled NBDE was spiked with 5 ppm by weight of TEMPO stabilizer. The stabilized NBDE was subjected to accelerated aging test conditions by heating to 80° C. for 6 days, followed by He purge to determine the amount of non-volatile residue as described in Example 3. The non-volatile residue for this run was 0.13 wt. %, corresponding to a degradation rate of 9 ppm per hour at 80° C. This represents a 96.5% decrease in the degradation rate relative to unstabilized NBDE. The experimental results are summarized in Table 1 and FIGS. 2 and 3.

Example 19

Evaluation of the Degradation Rate of NBDE at 80° C. Stabilized with 200 ppm of 4H-TEMPO Using Accelerated Aging Conditions A sample of NBDE was flash distilled to remove non-volatile impurities as described in Example 1. The distilled NBDE was spiked with 200 ppm by weight of 4H-TEMPO stabilizer. The stabilized NBDE was subjected to accelerated aging test conditions by heating to 80° C. for 6 days, followed by He purge to determine the amount of non-volatile residue as described in Example 3. This test was run in duplicate. The average non-volatile residue for these two runs was 0.10 wt. %, corresponding to a degradation rate of 7 ppm per hour at 80° C. This represents a 97.2% decrease in the degradation rate relative to unstabilized NBDE. The experimental results are summarized in Table 1 and FIGS. 2 and 3.

Example 20

Evaluation of the Degradation Rate of NBDE at 80° C. Stabilized with 20 ppm of 4H-TEMPO Using Accelerated Aging Conditions A sample of NBDE was flash distilled to remove non-volatile impurities as described in Example 1. The distilled NBDE was spiked with 20 ppm by weight of 4H-TEMPO stabilizer. The stabilized NBDE was subjected to accelerated aging test conditions by heating to 80° C. for 6 days, followed by He purge to determine the amount of non-volatile residue as described in Example 3. This test was run in duplicate. The average non-volatile residue for these two runs was 0.08 wt. %, corresponding to a degradation rate of 6 ppm per hour at 80° C. This represents a 97.8% decrease in the degradation rate relative to unstabilized NBDE. The experimental results are summarized in Table 1 and FIGS. 2 and 3.

Example 21

Evaluation of the Degradation Rate of NBDE at 60° C. Stabilized with 200 ppm of TEMPO Using Accelerated Aging Conditions A sample of NBDE was flash distilled to remove non-volatile impurities as described in Example 1. The distilled NBDE was spiked with 200 ppm by weight of TEMPO stabilizer. The stabilized NBDE was subjected to accelerated aging test conditions by heating to 60° C. for 7 days, followed by He purge to determine the amount of non-volatile residue as described in Example 3. This test was run in duplicate. The average non-volatile residue for these two runs was 0.02 wt. %, corresponding to a degradation rate of 1 ppm per hour at 80° C. This represents a 99.5% decrease in the degradation rate relative to unstabilized NBDE. The experimental results are summarized in Table 1 and FIGS. 2 and 3.

Example 22

Evaluation of the Degradation Rate of NBDE at 60° C. Stabilized with 50 ppm of TEMPO Using Accelerated Aging Conditions A sample of NBDE was flash distilled to remove non-volatile impurities as described in Example 1. The distilled NBDE was spiked with 50 ppm by weight of TEMPO stabilizer. The stabilized NBDE was subjected to accelerated aging test conditions by heating to 60° C. for 7 days, followed by He purge to determine the amount of non-volatile residue as described in Example 3. This test was run in duplicate. The average non-volatile residue for these two runs was 0.06 wt. %, corresponding to a degradation rate of 3 ppm per hour at 80° C. This represents a 98.7% decrease in the degradation rate relative to unstabilized NBDE. The experimental results are summarized in Table 1 and FIGS. 2 and 3.

Example 23

Evaluation of the Degradation Rate of NBDE at 60° C. Stabilized with 20 ppm of TEMPO Using Accelerated Aging Conditions A sample of NBDE was flash distilled to remove non-volatile impurities as described in Example 1. The distilled NBDE was spiked with 20 ppm by weight of TEMPO stabilizer. The stabilized NBDE was subjected to accelerated aging test conditions by heating to 60° C. for 7 days, followed by He purge to determine the amount of non-volatile residue as described in Example 3. This test was run in duplicate. The average non-volatile residue for these two runs was 0.03 wt. %, corresponding to a degradation rate of 2 ppm per hour at 80° C. This represents a 99.3% decrease in the degradation rate relative to unstabilized NBDE. The experimental results are summarized in Table 1 and FIGS. 2 and 3.

Example 24

Mixing of Aged Unstabilized NBDE with DEMS as a Polar Liquid

This example illustrates the forced precipitation of the non-polar oligomers by gradually increasing the net polarity of the liquid. Working in a nitrogen containing dry box, 102.0 g of unstabilized NBDE which had aged for 287 days at ambient temperature was placed into a 200 ml Pyrex bottle. The same weight of DEMS was placed into a second similar Pyrex bottle. Both the NBDE and DEMS were clear, colorless liquids with no indication of precipitate or residue. The two liquids were combined by slowly adding the DEMS to the NBDE. After the addition of about 20 g of DEMS a small amount of a white permanent precipitate was evident in the DEMS-NBDE mixture. This precipitate grew more prominent as the balance of the DEMS was added to the NBDE. The white precipitate gradually settled to the bottom of the Pyrex container. The contents of the Pyrex container were transferred to a Schlenk flask. The flask was subjected to dynamic vacuum for 4 hours at room temperature to remove the DEMS and NBDE liquids, leaving behind 1.20 g. of white solid. This weight of non-volatile solid residue corresponds to 1.18 wt. % based on the initial weight of the NBDE. This is equivalent to a degradation rate of 1.71 ppm per hour at ambient temperature. The weight percent residue determined by this route is in excellent agreement with the amount of residue measured by the He purge non-volatile residue test described in FIGS. 2 and 3.

Example 25

Evaluation of Precipitation in the Mixing of Aged Unstabilized NBDE with DEMS

NBDE was flash distilled to remove non-volatile impurities using a rotary-evaporator as described in Example 1. The distilled material was analyzed by GC to have a nominal purity of 99.4%. No stabilizer was added to the NBDE. The unstabilized NBDE was subjected to accelerated aging test conditions by heating to 80° C. for 7 days in quartz bubblers as described in Example 3. This test was done in duplicate using 87.64 g and 90.23 g of NBDE for the two runs. Upon removal of the two bubblers from the oven at 80° C. there was no visible sign of precipitation or discoloration of the NBDE liquid. After allowing the NBDE to cool to room temperature, DEMS was slowly added to each bubbler through the inlet line in an attempt to force the precipitation of dissolved oligomeric degradation products. The first permanent precipitate was visible after the addition of 35-40 g of DEMS to the unstabilized NBDE. Additional DEMS was added until each bubbler contained a 1:1 weight ratio of NBDE to DEMS. At this point a large amount of white precipitate was evident, indicating that a substantial amount of oligomeric degradation products were present. The bubblers were subjected to dynamic vacuum for 4 hours at 30° C., followed by a final evacuation for 1 hour at 80° C., leaving behind 0.73 g and 1.04 g of white solid residue. This amounts to an average non-volatile residue of 1.00% based on the initial weight of the NBDE, corresponding to a degradation rate of 59 ppm per hour at 80° C.

Example 26

Evaluation of Reduction of Precipitation in the Mixing of Aged NBDE with DEMS Stabilized with 200 ppm of HQMME NBDE was flash distilled to remove non-volatile impurities using a rotary-evaporator as described in Example 1. The distilled material was analyzed by GC to have a nominal purity of 99.4%. The NBDE was spiked with 200 ppm by weight of HQMME stabilizer. The stabilized NBDE was subjected to accelerated aging test conditions by heating to 80° C. for 7 days in quartz bubblers as described in Example 3. This test was done in duplicate using 98.77 g and 71.93 g of NBDE for the two runs. Upon removal of the two bubblers from the oven at 80° C. there was no visible sign of precipitation or discoloration of the NBDE liquid. After allowing the NBDE to cool to room temperature, DEMS was slowly added to each bubbler through the inlet line in an attempt to force the precipitation of dissolved oligomeric degradation products. The addition of DEMS continued until each bubbler contained a 1:1 weight ratio of NBDE to DEMS. This resulted in a faint, cloudy solution in each of the two bubblers, indicating precipitation of a small amount of oligomers from solution. The bubblers were subjected to dynamic vacuum for 4 hours at 30° C., followed by a final evacuation for 1 hour at 80° C., leaving behind 0.17 g and 0.14 g of white solid residue. This amounts to an average non-volatile residue of 0.18 wt. % based on the initial weight of the NBDE, corresponding to a degradation rate of 11 ppm per hour at 80° C. This represents an 82% decrease in the degradation rate relative to forced precipitation of the unstabilized NBDE subjected to identical ageing conditions as described in Example 13. The experimental results are summarized in Table 2.

Example 27

Evaluation of Reduction of Precipitation in the Mixing of Aged NBDE with DEMS Stabilized with 200 ppm of MHQ NBDE was flash distilled to remove non-volatile impurities using a rotary-evaporator as described in Example 1. The distilled material was analyzed by GC to have a nominal purity of 99.4%. The NBDE was spiked with 200 ppm by weight of MHQ stabilizer. The stabilized NBDE was subjected to accelerated aging test conditions by heating to 80° C. for 7 days in quartz bubblers as described in Example 3. This test was done in duplicate using 105.17 g and 98.53 g of NBDE for the two runs. Upon removal of the two bubblers from the oven at 80° C. there was no visible sign of precipitation or discoloration of the NBDE liquid. After allowing the NBDE to cool to room temperature, DEMS was slowly added to each bubbler through the inlet line in an attempt to force the precipitation of dissolved oligomeric degradation products. The addition of DEMS continued until each bubbler contained a 1:1 weight ratio of NBDE to DEMS. The resulting NBDE-DEMS blend remained clear and colorless with no visible indication of precipitation. The bubblers were subjected to dynamic vacuum for 4 hours at 30° C., followed by a final evacuation for 1 hour at 80° C., leaving behind 0.10 g and 0.03 g of white solid residue. This amounts to an average non-volatile residue of 0.06 wt. % based on the initial weight of the NBDE, corresponding to a degradation rate of 4 ppm per hour. This represents a 94% decrease in the degradation rate relative to forced precipitation of the unstabilized NBDE subjected to identical ageing conditions as described in Example 13. The experimental results are summarized in Table 2.

Example 28

Evaluation of Reduction of Precipitation in the Mixing of Aged NBDE with DEMS Stabilized with 200 ppm 22DH4MB NBDE was flash distilled to remove non-volatile impurities using a rotary-evaporator as described in Example 1. The distilled material was analyzed by GC to have a nominal purity of 99.4%. The NBDE was spiked with 200 ppm by weight of 22DH4MB stabilizer. The stabilized NBDE was subjected to accelerated aging test conditions by heating to 80° C. for 7 days in quartz bubblers as described in Example 3. This test was done in duplicate using 111.53 g and 106.22 g of NBDE for the two runs. Upon removal of the two bubblers from the oven at 80° C. there was no visible sign of precipitation or discoloration of the NBDE liquid. After allowing the NBDE to cool to room temperature, DEMS was slowly added to each bubbler through the inlet port in an attempt to force the precipitation of dissolved oligomeric degradation products. The addition of DEMS continued until each bubbler contained a 1:1 weight ratio of NBDE to DEMS. This resulted in a cloudy solution in each of the two bubblers, indicating some amount of precipitation of oligomers from solution. The bubblers were subjected to dynamic vacuum for 4 hours at 30° C., followed by a final evacuation for 1 hour at 80° C., leaving behind 0.51 g and 0.65 g of white solid residue. This equates to an average non-volatile residue of 0.53 wt. % based on the initial weight of the NBDE, corresponding to a degradation rate of 32 ppm per hour at 80° C. This represents a 46% decrease in the degradation rate relative to forced precipitation of the unstabilized NBDE subjected to identical ageing conditions as described in Example 25. The experimental results are summarized in Table 2.

Example 29

Evaluation of Reduction of Precipitation in the Mixing of Aged NBDE with DEMS Stabilized with 200 ppm of TEMPO NBDE was flash distilled to remove non-volatile impurities using a rotary-evaporator as described in Example 1. The distilled material was analyzed by GC to have a nominal purity of 99.4%. The NBDE was spiked with 200 ppm by weight of TEMPO stabilizer. The stabilized NBDE was subjected to accelerated aging test conditions by heating to 80° C. for 7 days in quartz bubblers as described in Example 3. This test was done in duplicate using 94.77 g and 110.56 g of NBDE for the two runs. Upon removal of the two bubblers from the oven at 80° C. there was no visible sign of precipitation. After allowing the NBDE to cool to room temperature, DEMS was slowly added to each bubbler through the inlet port in an attempt to force the precipitation of dissolved oligomeric degradation products. The addition of DEMS continued until each bubbler contained a 1:1 weight ratio of NBDE to DEMS. The resulting NBDE-DEMS blend remained clear with no visible indication of cloudiness or precipitation. The bubblers were subjected to dynamic vacuum for 4 hours at 30° C., followed by a final evacuation for 1 hour at 80° C., leaving behind 0.11 g and 0.10 g of yellowish residue. This equates to an average non-volatile residue of 0.10 wt. % based on the initial weight of the NBDE, corresponding to a degradation rate of 6 ppm per hour. This represents a 90% decrease in the degradation rate relative to forced precipitation of the unstabilized NBDE subjected to identical ageing conditions as described in Example 25. The experimental results are summarized in Table 2.

Example 30

Mixing of Aged Unstabilized NBDE with a Polar Solvent

Similar to Example 24, working in a nitrogen containing dry box, 2.0 ml (1.6 g) of isopropyl alcohol (IPA) was slowly added to 2.0 ml of the unstabilized NBDE (1.7 g). The NBDE used for this test was aged for 287 days at ambient temperature. Both the NBDE and IPA used for this experiment were clear, colorless liquids with no indication of precipitate or residue. An immediate permanent precipitate was noticed after the addition of the first few drops of isopropanol to the aged NBDE. The amount of precipitation became more pronounced as the remainder of the 2.0 ml of IPA was added. This example again demonstrates the precipitation of the largely non-polar oligomers caused by increasing the net polarity of the solvent.

Example 31

Characterization of NBDE Degradation Products

Figure 1:
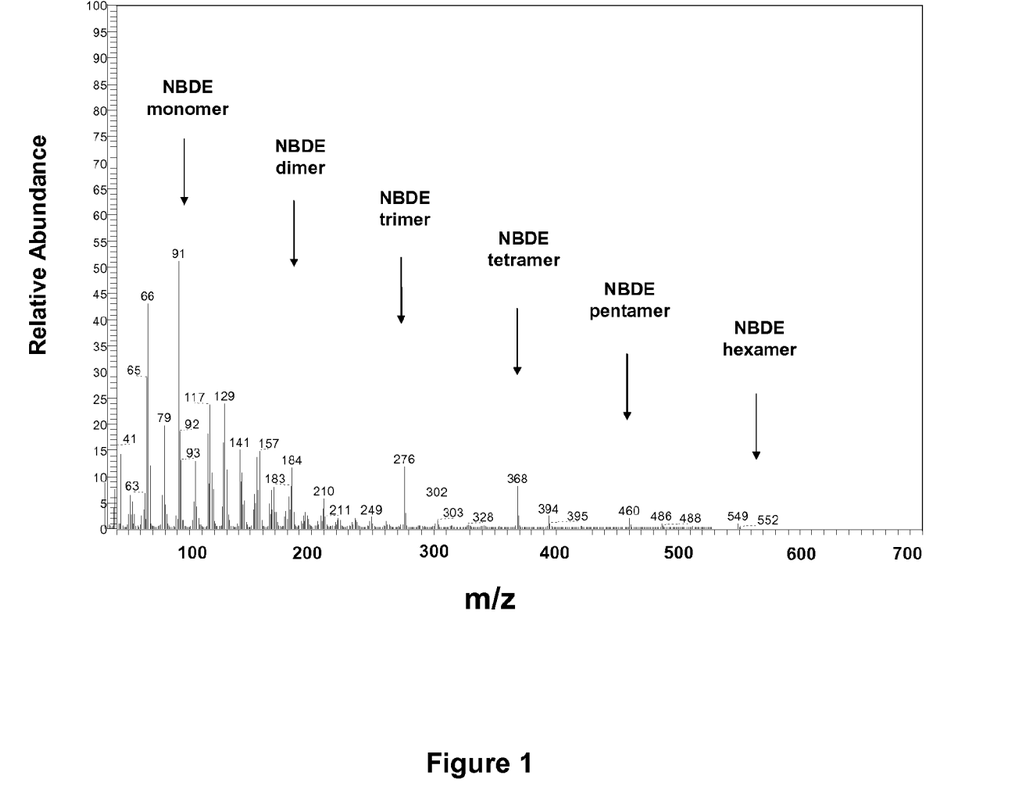
FIG. 1. Solids-probe mass spectrum of non-volatile residue collected from evaporation of an aged sample of NBDE.

A 50 g sample of unstabilized NBDE which had been stored at room temperature for several months was placed into a 100 ml quartz ampoule equipped with a Teflon valve. The ampoule was evacuated at room temperature for 2 hours to generate an off-white non-volatile residue. The resulting solid was collected and analyzed by solids-probe mass spectrometry. The analysis confirmed the presence of various oligomers of NBDE, including the dimer, trimer, tetramer, pentamer, hexamer, etc. The solids-probe mass spectrum from this analysis is shown in FIG. 1.

TABLE 1

Summary of the non-volatile residue test results described in Examples 1-23.

| Example No. | Stabilizer | Aging Conditions | Wt. of NBDE (g) | NVR (non-volatile residue) (g) | NVR (wt. %) | NVR avg (wt. %) | Degradation rate (ppm/hr) | Normalized degradation rate | Reduction of degradation rate (%) |
|---|---|---|---|---|---|---|---|---|---|
| 1 | no stabilizer | none | 619.32 | 0.59 | 0.10 | 0.05 | NA | NA | NA |
|  |  |  | 582.70 | 0.00 | 0.00 |  |  |  |  |
| 2 | no stabilizer | 287 days at RT | 202.46 | 2.29 | 1.13 | 1.12 | 1.63 | NA | NA |
|  |  |  | 202.15 | 2.24 | 1.11 |  |  |  |  |
| 3 | no stabilizer | 7 days at 80° C. | 148.35 | 6.25 | 4.21 | 4.33 | 258 | 1.000 | 0.0 |
|  |  |  | 149.79 | 6.06 | 4.05 |  |  |  |  |
|  |  |  | 103.87 | 5.59 | 5.38 |  |  |  |  |
|  |  |  | 118.95 | 5.94 | 4.99 |  |  |  |  |
|  |  |  | 148.30 | 5.31 | 3.58 |  |  |  |  |
|  |  |  | 149.15 | 5.65 | 3.79 |  |  |  |  |
| 4 | 200 ppm BHT | 7 days at 80° C. | 149.44 | 4.6 | 3.08 | 3.01 | 179 | 0.690 | 31.0 |
|  |  |  | 163.89 | 4.83 | 2.95 |  |  |  |  |
| 5 | 200 ppm TBC | 7 days at 80° C. | 155.43 | 3.43 | 2.21 | 2.64 | 157 | 0.609 | 39.1 |
|  |  |  | 154.63 | 4.75 | 3.07 |  |  |  |  |
| 6 | 200 ppm TBC with $O_2$ | 7 days at 80° C. | 174.10 | 1.51 | 0.87 | 0.97 | 57 | 0.223 | 77.7 |
|  |  |  | 164.59 | 1.75 | 1.06 |  |  |  |  |
| 7 | 200 ppm MHQ | 7 days at 80° C. | 154.95 | 1.14 | 0.74 | 0.79 | 47 | 0.183 | 81.7 |
|  |  |  | 146.14 | 1.24 | 0.85 |  |  |  |  |
| 8 | 200 ppm MHQ with $O_2$ | 7 days at 80° C. | 152.93 | 0.52 | 0.34 | 0.39 | 23 | 0.089 | 91.1 |
|  |  |  | 145.57 | 0.63 | 0.43 |  |  |  |  |
| 9 | 200 ppm HQMME | 7 days at 80° C. | 106.26 | 1.00 | 0.94 | 0.90 | 53 | 0.207 | 79.3 |
|  |  |  | 114.82 | 0.98 | 0.85 |  |  |  |  |
| 10 | 50 ppm HQMME | 7 days at 80° C. | 110.75 | 1.20 | 1.08 | 1.42 | 84 | 0.327 | 67.3 |
|  |  |  | 130.23 | 2.28 | 1.75 |  |  |  |  |
| 11 | 500 ppm HQMME | 7 days at 80° C. | 209.14 | 3.62 | 1.73 | 1.73 | 103 | 0.399 | 60.1 |
| 12 | 200 ppm 2H4MB | 7 days at 80° C. | 147.78 | 0.59 | 0.40 | 0.33 | 20 | 0.077 | 92.3 |
|  |  |  | 154.91 | 0.41 | 0.26 |  |  |  |  |
| 13 | 200 ppm 24DHB | 7 days at 80° C. | 149.14 | 0.32 | 0.21 | 0.21 | 12 | 0.048 | 95.2 |
|  |  |  | 145.25 | 0.29 | 0.20 |  |  |  |  |
| 14 | 200 ppm 22DH4MB | 7 days at 80° C. | 152.00 | 0.31 | 0.20 | 0.21 | 13 | 0.049 | 95.1 |
|  |  |  | 165.88 | 0.37 | 0.22 |  |  |  |  |
| 15 | 200 ppm TEMPO | 7 days at 80° C. | 140.51 | 0.04 | 0.03 | 0.02 | 1 | 0.006 | 99.4 |
|  |  |  | 148.59 | 0.03 | 0.02 |  |  |  |  |
| 16 | 50 ppm TEMPO | 7 days at 80° C. | 143.38 | 0.08 | 0.06 | 0.04 | 3 | 0.010 | 99.0 |
|  |  |  | 139.63 | 0.04 | 0.03 |  |  |  |  |
| 17 | 20 ppm TEMPO | 7 days at 80° C. | 130.45 | 0.17 | 0.13 | 0.10 | 6 | 0.023 | 97.7 |
|  |  |  | 144.58 | 0.10 | 0.07 |  |  |  |  |
| 18 | 5 ppm TEMPO | 6 days at 80° C. | 68.82 | 0.09 | 0.13 | 0.13 | 9 | 0.035 | 96.5 |
| 19 | 200 ppm 4H-TEMPO | 6 days at 80° C. | 137.56 | 0.12 | 0.09 | 0.10 | 7 | 0.028 | 97.2 |
|  |  |  | 116.36 | 0.14 | 0.12 |  |  |  |  |
| 20 | 20 ppm 4H-TEMPO | 6 days at 80° C. | 130.98 | 0.15 | 0.11 | 0.08 | 6 | 0.022 | 97.8 |
|  |  |  | 102.25 | 0.05 | 0.05 |  |  |  |  |
| 21 | 200 ppm TEMPO | 7 days at 60° C. | 130.38 | 0.03 | 0.02 | 0.02 | 1 | 0.005 | 99.5 |
|  |  |  | 172.71 | 0.03 | 0.02 |  |  |  |  |
| 22 | 50 ppm TEMPO | 7 days at 60° C. | 147.10 | 0.12 | 0.08 | 0.06 | 3 | 0.013 | 98.7 |
|  |  |  | 155.90 | 0.05 | 0.03 |  |  |  |  |
| 23 | 20 ppm TEMPO | 7 days at 60° C. | 154.92 | 0.03 | 0.02 | 0.03 | 2 | 0.007 | 99.3 |
|  |  |  | 167.67 | 0.07 | 0.04 |  |  |  |  |

TABLE 2

Summary of the non-volatile residue test results from the forced precipitation experiments described in Examples 25-29.

| Example No. | Stabilizer | Ageing Conditions | Wt. of NBDE (g) | Wt. of DEMS added (g) | NVR (non-volatile residue) (g) | NVR (wt. %) | NVR avg (wt. %) | Degradation rate (ppm/hr) | Normalized degradation rate | Reduction of degradation rate (%) |
|---|---|---|---|---|---|---|---|---|---|---|
| 25 | none | 7 days at 80° C. | 87.64 | 87.64 | 1.04 | 1.19 | 1.00 | 59 | 1.00 | 0.00 |
|  |  |  | 90.23 | 90.23 | 0.73 | 0.81 |  |  |  |  |
| 26 | 200 ppm HQMME | 7 days at 80° C. | 98.77 | 98.77 | 0.17 | 0.17 | 0.18 | 11 | 0.18 | 0.82 |
|  |  |  | 71.93 | 71.93 | 0.14 | 0.19 |  |  |  |  |
| 27 | 200 ppm MHQ | 7 days at 80° C. | 94.77 | 94.77 | 0.10 | 0.10 | 0.06 | 4 | 0.06 | 0.94 |
|  |  |  | 110.56 | 110.56 | 0.03 | 0.03 |  |  |  |  |

TABLE 2-continued

Summary of the non-volatile residue test results from the forced precipitation experiments described in Examples 25-29.

| Example No. | Stabilizer | Ageing Conditions | Wt. of NBDE (g) | Wt. of DEMS added (g) | NVR (non-volatile residue) | | avg (wt. %) | Degradation rate (ppm/hr) | Normalized degradation rate | Reduction of degradation rate (%) |
|---|---|---|---|---|---|---|---|---|---|---|
| | | | | | (g) | (wt. %) | | | | |
| 28 | 200 ppm 22DH4MB | 7 days at 80° C. | 111.53 106.22 | 111.53 106.22 | 0.51 0.65 | 0.46 0.61 | 0.53 | 32 | 0.54 | 0.46 |
| 29 | 200 ppm TEMPO | 7 days at 80° C. | 94.77 110.56 | 94.77 110.56 | 0.11 0.10 | 0.12 0.09 | 0.10 | 6 | 0.10 | 0.90 |

The embodiments of the present invention listed above, including the working examples, are exemplary of numerous embodiments that may be made of the present invention. It is contemplated that numerous other configurations of the process may be used, and the materials used in the process may be selected from numerous materials other than those specifically disclosed. In short, the present invention has been set forth with regard to particular embodiments, but the full scope of the present invention should be ascertained from the claims as follow.

The invention claimed is:

1. A stabilized composition consisting essentially of an unsaturated hydrocarbon-based precursor material, and a nitroxyl radical based stabilizer; wherein
the unsaturated hydrocarbon-based precursor material is selected from the group consisting of 2,5-Norbornadiene (NBDE) and Norbornene; and
the nitroxyl radical based stabilizer has a structure:

wherein:
raised period "•" denotes one unpaired electron;
$R^1$ through $R^4$ are independently selected from a straight chained or branched, substituted or unsubstituted, alkyl or alkenyl group; wherein the substituted group comprises oxygen-containing groups selected from the group consisting of hydroxyl, carbonyl, alkoxide, and carboxylic group; and
$R^5$ and $R^6$ are independently selected from a straight chained or branched, a substituted or unsubstituted, alkyl group or alkenyl group.

2. The composition of claim 1, wherein the unsaturated hydrocarbon-based precursor material is 2,5-Norbornadiene (NBDE).

3. The composition of claim 1, wherein the alkyl group or the alkenyl group in $R^5$ and $R^6$ is connected by a bridging group to form a cyclical structure of saturated, partially unsaturated or aromatic ring.

4. The composition of claim 1, wherein $R^1$ through $R^4$ each is selected from the group consisting of methyl, ethyl, n-propyl, n-butyl, n-pentyl, iso-propyl, iso-butyl, iso-pentyl, tert-butyl, neo-pentyl, octadecyl, propenyl, butenyl, pentenyl and combinations thereof.

5. The composition of claim 1, wherein $R^5$ and $R^6$ each is selected from the group consisting of methyl, ethyl, n-propyl, n-butyl, n-pentyl, iso-propyl, iso-butyl, iso-pentyl, tert-butyl, neo-pentyl, octadecyl, propenyl, butenyl, pentenyl, and part of a cyclic structure and its substituted cyclic structure of 6-membered piperidine or 5-membered pyrrolidones.

6. The composition of claim 1, wherein the stabilizer is the nitroxyl radical based stabilizer selected from the group consisting of 2,2,6,6-tetramethyl-1-piperidinyloxy (TEMPO), 4-hydroxy-2,2,6,6-tetramethyl-1-piperidinyloxy (4H-TEMPO), di-tert-butyl nitroxyl, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl 4-tert-butylbenzoate, bis(1-oxyl-2,2,6,6-tetramethylpiperidin-4-yl)succinate, bis(1-oxyl-2,2,6,6-tetramethylpiperidin-4-yl)adipate, bis(1-oxyl-2,2,6,6-tetramethylpiperidin-4-yl)sebacate, bis (1-oxyl-2,2,6,6-tetramethylpiperidin-4-yl)n-butylmalonate, bis(1-oxyl-2,2,6,6-tetramethylpiperidin-4-yl)phthalate, bis (1-oxyl-2,2,6,6-tetramethylpiperidin-4-yl)isophthalate, bis (1-oxyl-2,2,6,6-tetramethylpiperidin-4-yl)terephthalate, bis (1-oxyl-2,2,6,6-tetramethylpiperidin-4-yl) hexahydroterephthalate, N,N'-bis(1-oxyl-2,2,6,6-tetramethylpiperidin-4-yl)adipamide, N-(1-oxyl-2,2,6,6-tetramethylpiperidin-4-yl)-caprolactam, N-(1-oxyl-2,2,6,6-tetramethylpiperidin-4-yl)-dodecylsuccinimide, 2,4,6-tris(1-oxyl-2,2,6,6-tetramethylpiperidin-4-yl isocyanurate, 2,4,6-tris[N-butyl-N-(1-oxyl-2,2,6,6-tetramethylpiperidin-4-yl]-s-triazine, 4,4'-ethylenebis(1-oxyl-2,2,6,6-tetramethylpiperazin-3-one) and combinations thereof.

7. The composition of claim 1, wherein the stabilizer is the nitroxyl radical based stabilizer selected from the group consisting of 2,2,6,6-tetramethyl-1-piperidinyloxy (TEMPO) and 4-hydroxy-2,2,6,6-tetramethyl-1-piperidinyloxy (4H-TEMPO).

* * * * *